United States Patent [19]

Sammons et al.

[11] Patent Number: 5,073,963
[45] Date of Patent: Dec. 17, 1991

[54] COMPUTERIZED METHOD OF MATCHING TWO-DIMENSIONAL (2-D) PATTERNS

[75] Inventors: David W. Sammons; Wen-Jeng Ko; Yi-Cheng Liu, all of Tucson, Ariz.

[73] Assignee: Arizona Technology Development Corp., Tucson, Ariz.

[21] Appl. No.: 528,816
[22] Filed: May 25, 1990
[51] Int. Cl.$^5$ .................... G06K 9/62; G06K 9/00; G06F 15/00
[52] U.S. Cl. ..................... 382/30; 382/6; 382/44; 358/111; 364/413.01; 364/413.13
[58] Field of Search .............. 382/6, 30, 44; 364/413.13, 413.01; 358/111

[56] References Cited

U.S. PATENT DOCUMENTS

| | | | |
|---|---|---|---|
| 4,389,670 | 6/1983 | Davidson et al. | 358/111 |
| 4,590,607 | 5/1986 | Kauth | 382/41 |
| 4,618,937 | 10/1986 | Elias et al. | 364/518 |
| 4,638,456 | 1/1987 | Elias et al. | 364/518 |
| 4,644,582 | 2/1987 | Morishita et al. | 382/44 |
| 4,706,192 | 11/1987 | Nasu et al. | 364/413.01 |
| 4,741,043 | 4/1988 | Bacus | 382/6 |
| 4,811,218 | 3/1989 | Hunkapiller et al. | 364/413.01 |
| 4,812,909 | 3/1989 | Yokobayashi et al. | 358/183 |
| 4,825,388 | 4/1989 | Dailey et al. | 364/518 |
| 4,894,786 | 1/1990 | Hara | 364/413.01 |
| 4,920,089 | 5/1986 | Hartman | 382/6 |
| 4,956,872 | 9/1990 | Kimura | 382/44 |

OTHER PUBLICATIONS

Article by P. F. Lemkin et al., entitled "GELLAB: A Computer System for 2D Gel Electrophoresis Analysis, II. Pairing Spots", Computers and Biomedical Research, vol. 14, pp. 355-380 (1981).
Article by K. P. Vo et al., entitled "Computer Analysis of Two-Dimensional Gels", Analytical Biochemistry vol. 112, pp. 258-271 (1981).
Article by M. J. Miller et al., entitled "Computer Analysis of Two-Dimensional Gels; Semi-Automatic Matching", Clin. Chem. vol 28/4, pp. 867-875 (1982).
Article by M. J. Miller et al, entitled "Computer Analysis of Two-Dimensional Gels: Automatic Matching", Electrophoresis vol. 5, pp. 297-303 (1984).
Article by P. Vincens et al., entitled "HERMS: A second generation approach to the automatic analysis of two-dimenesional electrophoresis gels, Part III: Spot list matching", Electrophoresis vol. 8, pp. 100-107 (1987).
Article by A. D. Olson et al., entitled "Elsie 4: Quantitative Computer Analysis of Sets of Two-Dimensional Gel Electrophoretograms", Analytical Biochemistry vol. 169, pp. 49-70 (1988).
M. M. Skolnick et al., entitled "An Algorithm for Comparing Two-Dimensional Electrophoretic Gels, with Particular Reference to the Study of Mutations", Advances in Human Genetics, vol. 16, Chapter 2, pp. 55-160, H. Harris & K. Hirschorn, Editors, (Plenum N.Y. 1986).
Article by AM. M. Skolnick et al., entitled "Computer Programs for Adapting Two-Dimensional Gels to the Study of Mutation", Clin. Chem. vol. 28/4, pp. 969-978 (1982).

*Primary Examiner*—Leo H. Boudreau
*Assistant Examiner*—Steven D. Fallon
*Attorney, Agent, or Firm*—Victor Flores

[57] ABSTRACT

This invention teaches a computerized method for use in data acquisition and manipulation of two-dimensional patterns in the fields of medicine, astronomy, chemistry, biology and biotechnology. The invention teaches an interactive computerized method for matching visual patterns of polypeptide spots in two-dimensional (2-D) gel electrophoretogram solubilized into polypeptide constituents that are separated by electrophoresis. The computerized method manipulates spot pixel coordinates using staged coordinate transformation techniques on spot markers and unknown study spots to reduce gel preparation distortions and allows a user to produce matching results in a manner that compares the transformed spot data using either a single reference gel or multiple reference gels approach for producing the matching results. The method also includes a spot matching verification step and a step to extract potentially mis-matched spots from reported matching results. The user can also resolve contradictions and perform spot matching analysis using isoelectric focusing (PI), and molecular weight (MW) dimensional separation data.

22 Claims, 15 Drawing Sheets

Microfiche Appendix Included
(5 Microfiche, 88 Pages)

COMPUTERIZED METHOD OF MATCHING TWO-DIMENSIONAL (2-D) PATTERNS

MICROFICHE APPENDIX

This patent application contains reference computer program listings and related material in the form of five (5) microfiche appendices A-E, containing a total of 88 frames.

FIELD OF THE INVENTION

This invention relates to computerized methods for data acquisition and manipulation of two-dimensional patterns in the fields of medicine, astronomy, chemistry, biology and biotechnology. More particularly, the present invention relates to computerized methods for data manipulation of visual patterns of polypeptide spots in one-dimension (1-D) and two-dimensional (2-D) gel electrophoretograms, i.e. visual patterns of protein of cells (tissue, or body fluids), solubilized into polypeptide constituents that are separated by electrophoresis. Even more particularly, the present invention relates to interactive computerized methods of spot data acquisition and pixel coordinate manipulation involving coordinate transformation techniques and the use of isoelectric focusing (PI), and molecular weight (MW) dimensional separation properties during a spot matching task.

DESCRIPTION OF THE PRIOR ART

In the biotechnology field, two-dimensional electrophoresis of polypeptides in polyacrylamide gel is a process known for separating the polypeptides, hereinafter also referred to as spots, in two dimensions, the first on the basis of charge by isoelectric focusing, the second on the basis of molecular weight by electrophoresis. The resulting two-dimensional gel electrophoretograms from this process contain spot patterns that are useful for analyzing cell types as well as the genetic metabolic activity of cells. Since the gels contain thousands of two-dimensional spot patterns having geometric characteristics that need to be visualized and manipulated for gel comparisons, the need for the computational and organizational power of a computer system is apparent. The visualization of the spots on the gel has been made possible by autoradiography or staining techniques, silver-stained electrophoretograms producing adequate gel scanning data for analysis, although considered less accurate than autoradiograms. The efficiency of the results of a spot pattern matching analysis is measured in percentages of matched spots between gels and depends greatly on the accuracy and robustness of the underlying computer program that controls data acquisition, spot detection and spot pattern data comparison and matching tasks. Limitations in the accuracy of data acquisition from gel images are known to involve several factors including film noise, flaws in the gels, which may include localized stretching or actual physical breaks in the gels, streaking, which are protein complexes formed during gel preparations and other positional related distortions caused by added or subtracted charges that affect mobility of the protein in the gel or intensity related distortions caused by faintly staining proteins due to heterozygosity characteristics of a spot. Certainly, human intervention and introduction of artifactual informalities also factors into the equation of optimizing the matching task. Further, the equipment used to create gel images from which the positional and intensity data is obtained must also be scrutinized in optimizing the spot matching tasks.

The importance of pursuing and improving quantitative analysis of two-dimensional gels has been recognized in the biotechnology community and has produced the following prior art publications and patents that are of interest in considering the present invention.

For example, an article by P. F. Lemkin et al. entitled "GELLAB: A Computer System for 2D Gel Electrophoresis Analysis. II. Pairing Spots", Computers and Biomedical Research, Vol. 14, pp. 355-380 (1981) teaches a spot-pairing algorithm and the establishment of landmark spots that aid in establishing a landmark region, spots within this landmark region are then compared in order to perform the spot pairing task.

An article by K. P. Vo et al, entitled "Computer Analysis of Two-Dimensional Gels", Analytical Biochemistry Vol. 112, pgs. 258-271 (1981), teaches a series of computer programs and procedures that manipulates intensity and positional data with improvements in the treatment of background film density and estimating the protein content of each spot. The data acquisition results obtained by operation of the computer program and procedures are typical data used in matching spots in gels and include: a contour number, the background value, the center of mass x-y coordinates, the area of the spot, the integrated density and the maximum scanner reading in the spot. The Vo et al. article notes an unresolved problem of overlapping spots that incorrectly positions a spot in the split area.

An article by M. M. Skolnick et al., entitled "Computer Programs for Adapting Two-Dimensional Gels to the Study of Mutation", Clin. Chem. Vol. 28/4, pp. 969-978 (1982), teaches a neighborhood transformation to digitized gel images. The transformation changes the digitized intensity value at each pixel (x and y coordinates) of an image to a new value, based solely upon a function of the immediate neighbors and the intensity value of the initial pixel.

An article by M. J. Miller et al, entitled "Computer Analysis of Two-Dimensional Gels: Semi-Automatic Matching", Clin. Chem. Vol. 28/4, pgs. 867-875 (1982), recognizes problems in detecting spots for reasons as listed above, and teaches the use of an interactive computer graphics to match spots of two gels.

An article by M. J. Miller et al, entitled "Computer Analysis of Two-Dimensional Gels: Automatic Matching", Electrophoresis Vol. 5, pgs. 297-303 (1984), teaches a matching algorithm based on hierarchical nearest neighbor analysis including primary and secondary cluster matching, consistency checking and transformation of the coordinate system of one gel into the coordinate space of another for any unmatched spots. The teaching assumes ideal gels having noise and streaking problems minimized.

An article by P. Vincens et al, entitled "HERMeS: A second generation approach to the automatic analysis of two-dimensional electrophoresis gels, Part III: Spot list matching", Electrophoresis Vol. 8, pgs. 100-107 (1987), teaches a method of matching spot patterns based on syntactic pattern recognition techniques which are based on non-metric considerations and describes a spot pattern observed on a given gel in a nongeometric way. The article is of particular interest in its recognition of limitations in programs that use geometric global corrections for correcting positional problems known to be encountered in two-dimensional gels.

An article by A. D. Olson et al, entitled "Elsie 4: Quantitative Computer Analysis of Sets of Two-Dimensional Gel Electrophoretograms", Analytical Biochemistry Vol. 169, pgs. 49–70 (1988), teaches the enhancement of the system described by Vo et al., discussed above, by utilization of high performance computing and imaging equipment for scanning gels, finding spots on the gel, measuring spot intensity, and quantitative evaluation of the analysis and matching the spots. The matching step utilize the same approach of matching by primary and secondary cluster described by M. J. Miller et al. above. The enhancements are directed at improved accuracy, portability, automation and speed.

M. M. Skolnick et al., Chapter entitled "An Algorithm for Comparing Two-Dimensional Electrophoretic Gels, with Particular Reference to the Study of Mutations", in *Advances in Human Genetics*, Vol. 16, Chapter 2, pgs. 55–160, H. Harris & K. Hirschorn, Editors, (Plenum N.Y. 1986), provides an excellent tutorial of the theory and practice of two-dimensional gels since the development of the technique in 1975. The algorithm introduced in the article follows basically the same steps as taught by Vo et al. but differs in the treatment of the location of spots by the use of a mathematical framework known as mathematical morphology as disclosed by M. M. Skolnick et al., in an article entitled "Computer Programs for Adapting Two-Dimensional Gels to the Study of Mutation", Clin. Chem. Vol. 28/4, pp. 969–978 (1982), discussed above. Further, the article introduces the positional noise function, identified by the symbol "omega", for better registration of two images during a linear transformation matching step. More importantly, the article emphasizes the limitations in the results of matching gels, even when considering "omega", in that the "omega" function could be decomposed into its vertical and horizontal components to factor the molecular weight and isoelectric point effects on the positioning of a spot on a gel, see p. 128 of the article, however, there is no teaching how this may be accomplished.

The prior art patents that relate to the field of the present invention concern computerized apparatus and method for spot quantitation, spot analysis, image data correspondence, spot detection, image analysis and comparison, all utilizing pixel x and y coordinate data as the primary physical characteristic of the spot or image. Included in the above teachings are U.S. Pat. Nos. 4,638,456, 4,618,937, 4,592,089, 4,590,607, 4,389,670, 4,812,909, 4,811,218, 4,706,192, 4,741,043 and 4,825,388. U.S. Pat. No. 4,590,607 teaches a method of detecting correspondence between multiple frames of image data, employing a serial neighborhood processing system while typical spot analysis methodology is found in the teachings of U.S. Pat. No. 4,592,089 which provides an analytical imaging processing system and method for analyzing spots on color electrophoretograms. The patent teaches a method of spot selection, quantification and visual confirmation to the user as to the exact boundaries of the spot pixel values that are used during the analysis. The analysis employs a series of processing steps using segmentation and quantification algorithms in the system software to manipulate spot physical characteristics, i.e. x and y coordinate position of the spot centroid, maximum spot dimensions in the x and y direction and the spot area within the interpreted boundary.

Although there have been many computerized advances in matching spots in 2-D gels, the prior art does not teach using staged coordinate transformations that firstly puts all of the designated marker spots that highlight a region or investigative pattern formed by spots in the gels being analyzed into a registered relationship with marker spots in a designated reference gel, and that secondly, applies the resulting marker spot registration relationship data to the coordinates of the remaining spots bounded by the marker spots, designated hereinafter as the unknown study spot members, to achieve x-y spot localization in the study gels having gel preparation distortional effects reduced to enable improved accuracy in spot location comparisons and improved matching efficiencies. Nor does the prior art teach the use of PI and MW gel preparation data in spot analysis of 2-D gels to improve spot matching interpretation between two or more 2-D gels.

Therefore, a need is believed to exist for an improved interactive computerized method of analyzing two-dimensional gel electrophoretograms that compensates for gel preparation distortional effects using staged coordinate transformation techniques prior to comparing and matching polypeptide spots contained in the 2-D gels.

Further, a need is seen to exist for an interactive computerized method for analyzing 2-D gels that uses staged coordinate transformation techniques and that also utilizes PI and MW preparation data that enables a user to combine the improved spot localization results associated with the transformation technique with the inherent accuracy associated with the PI and MW dimensional separation values that are at the heart of the electrophoresis process.

A need is seen to exist for an interactive computerized method for analyzing 2-D gels that utilizes the transformed spot data resulting from the staged coordinate transformation technique and that further performs matching verification steps to assure that reported matching spots are indeed within target geometrical boundaries.

A further need is seen to exist for an interactive computerized method for analyzing 2-D gels whereby a user can extract potentially mismatched set of spots to improve the accuracy of reported matching results.

In the broader sense, a need is seen to exist for a computerized method for analyzing 2-D patterns in the fields of medicine, astronomy, chemistry, biology and biotechnology that uses staged coordinate transformation, matching verification and matching techniques that improve the accuracy and efficiency of a 2-D pattern matching task.

SUMMARY OF THE INVENTION

Accordingly, the primary object of the present invention is to provide a computerized method of matching 2-D image data in the fields of medicine, astronomy, chemistry, biology and biotechnology having inherent distortional effects resulting from the initial image preparation process.

A specific object of the present invention is to provide an interactive computerized method of matching polypeptide spots in 2-D gels having inherent distortional effects resulting from the initial 2-D gel preparation process.

Another specific object of the present invention is to provide an interactive computerized method for resolving spot matching contradictions in spot clusters that inadvertently result during the comparing and matching steps.

Yet another specific object of the present invention is to provide an interactive computerized method for analyzing 2-D gels whereby a user can extract potentially mismatched set of spots to improve the accuracy of reported matching results.

A related object of the present invention is to provide PI and MW data for the 2-D gel spots being manipulated for use during an analysis of output data resulting from the comparing and matching subroutines to provide improved interpretation of the spot matching results.

According to one aspect of the invention, the foregoing objects are accomplished by a computerized method whereby each 2-D gel under investigation is scanned to generate an initial data file listing each spot's identification, the gel's name, each spot's original x-y coordinate values, each spot's integrated intensity, each spot's area, height and width. The user then designates one of the 2-D gels as a reference gel and the remaining gels as study gels and further designates in each gel, an investigative spot pattern of interest having a sufficient number of similarly positioned spots, generally prominent spots, referred to herein as reference marker spots in the reference gel and as study marker spots in the remaining study gels. The reference marker spots and the study marker spots form a boundary for the other spots within the spot patterns which are further designated as the unknown reference spots for the bounded spots in the reference gel and as unknown study spots for the bounded spots in the study gels. The user then further includes PI and MW for the designated reference and study marker spots in each of the gels for later utilization. At this point the user has effectively generated a modified initial data file for the scanned gels.

Using the modified initial data files, the user then executes several subroutines that: (1) adjust the original x-y coordinates of the spots in the investigative spot patterns in all gels by utilizing a two-stage coordinate transformation step and an interpolation step using the marker PI and MW data, (2) compare spot coordinates in a reference gel with spot coordinates in each study gel (referred to as a single reference match) to determine potentially matching pairs of spots, or that compare spot coordinates in one gel with spot coordinates in the other gels, each time using one of the gels, including the previously designated reference gel, as a reference gel (referred to as multiple reference match), also to determine potentially matching pairs of spots, (3) perform a verification step that vectorially manipulates the potentially matching spot pair data to acertain whether a match spot pair or a non-matching spot pair exists, (4) resolve contradicting matching results, (5) compare matched spot data results against potentially mismatched spot data and potentially correctly matched spot data to improve accuracy, efficiency and confidence level of the matching results, and (6) that enables a user to manipulate the various data bases resulting from the operation of the subroutines for verifying the results as well as analyzing the data from different perspectives.

Therefore, to the accomplishments of the foregoing objects, the invention consists of the foregoing features hereinafter fully described and particularly pointed out in the claims, the accompanying drawings and the following disclosure describing in detail the invention, such drawings and disclosure illustrating but one of the various ways in which the invention may be practiced.

BRIEF DESCRIPTION OF THE DRAWINGS:

FIG. 7a is a corresponding windowed spot pattern for gel "a" illustrated in FIG. 6a.

DESCRIPTION OF THE PREFERRED EMBODIMENT

Figure 1:
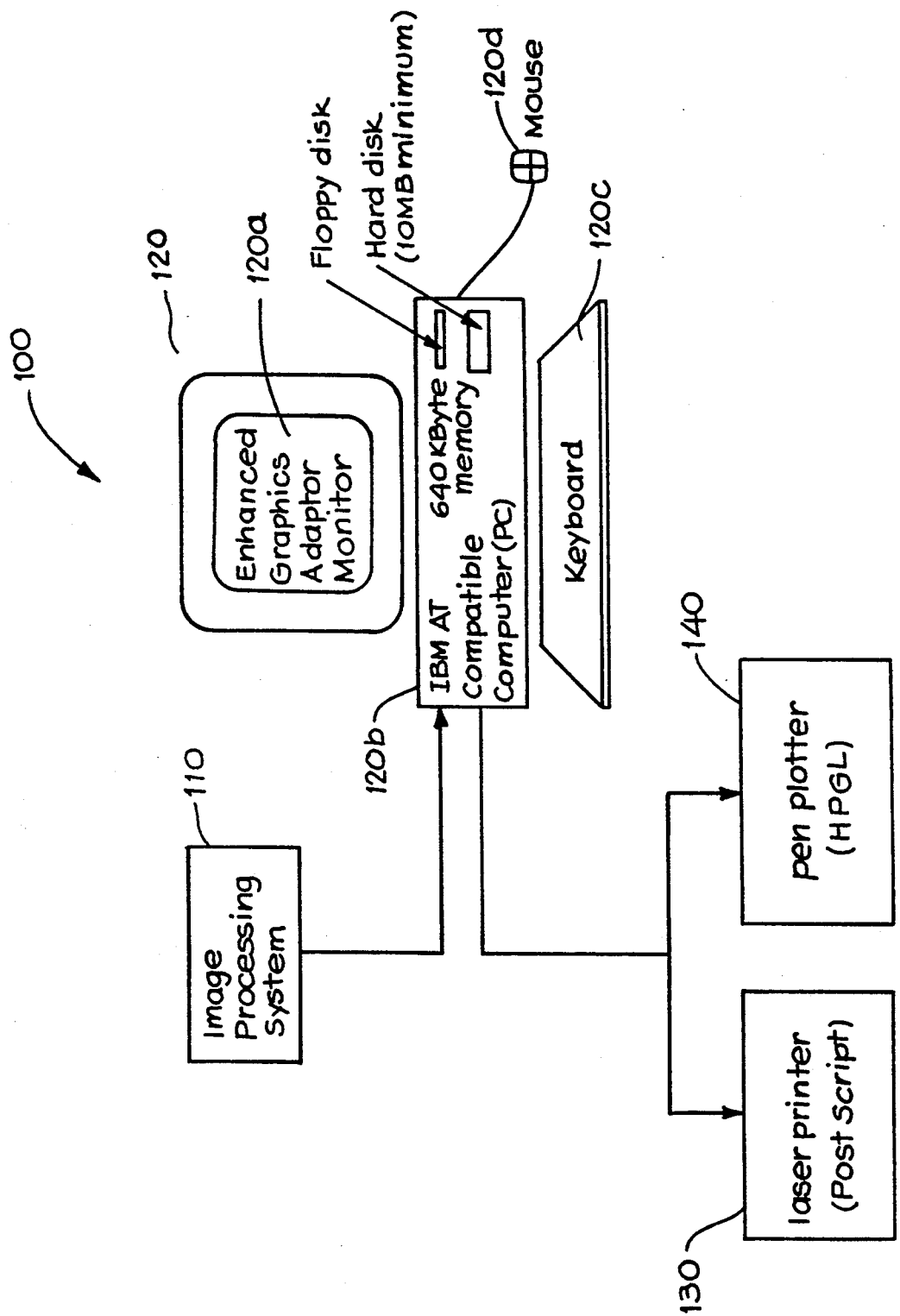
FIG. 1 illustrates a typical hardware configuration for performing the interactive computerized method of matching protein spot patterns in 2-D gels in accordance with the present invention.

Referring first to FIG. 1 where a typical computer workstation 100 is illustrated as a means for performing the spot matching task of the present invention. System 100 includes a gel image processing system 110, commercially available under the trademark "VISAGE", a personal computer 120, such as a commercially available "IBM AT", or compatible, having a minimum system configuration, shown as unit 120b, of 640 kilobytes of random access memory, floppy disk storage capability, 10 mega-bytes of hard disk storage and enhanced graphics adapter card. Unit 120b is coupled to a display monitor 120a having color graphic display capability, a keyboard 120c, a mouse 120d for cursor manipulation. Output from the personal computer 120 can be by means of printer 130 for text data/geographical data and a plotter 140 for graphical display data. In the preferred embodiment printer 130 is a laser printer adapted for PostScript format, such as a Silentwriter LC 890, commercially available from NEC. Also, in the preferred embodiment, plotter 140 is a plotter compatible with HPGL graphic plotting format, commercially available as a FACIT 4550/4551.

Figure 2:
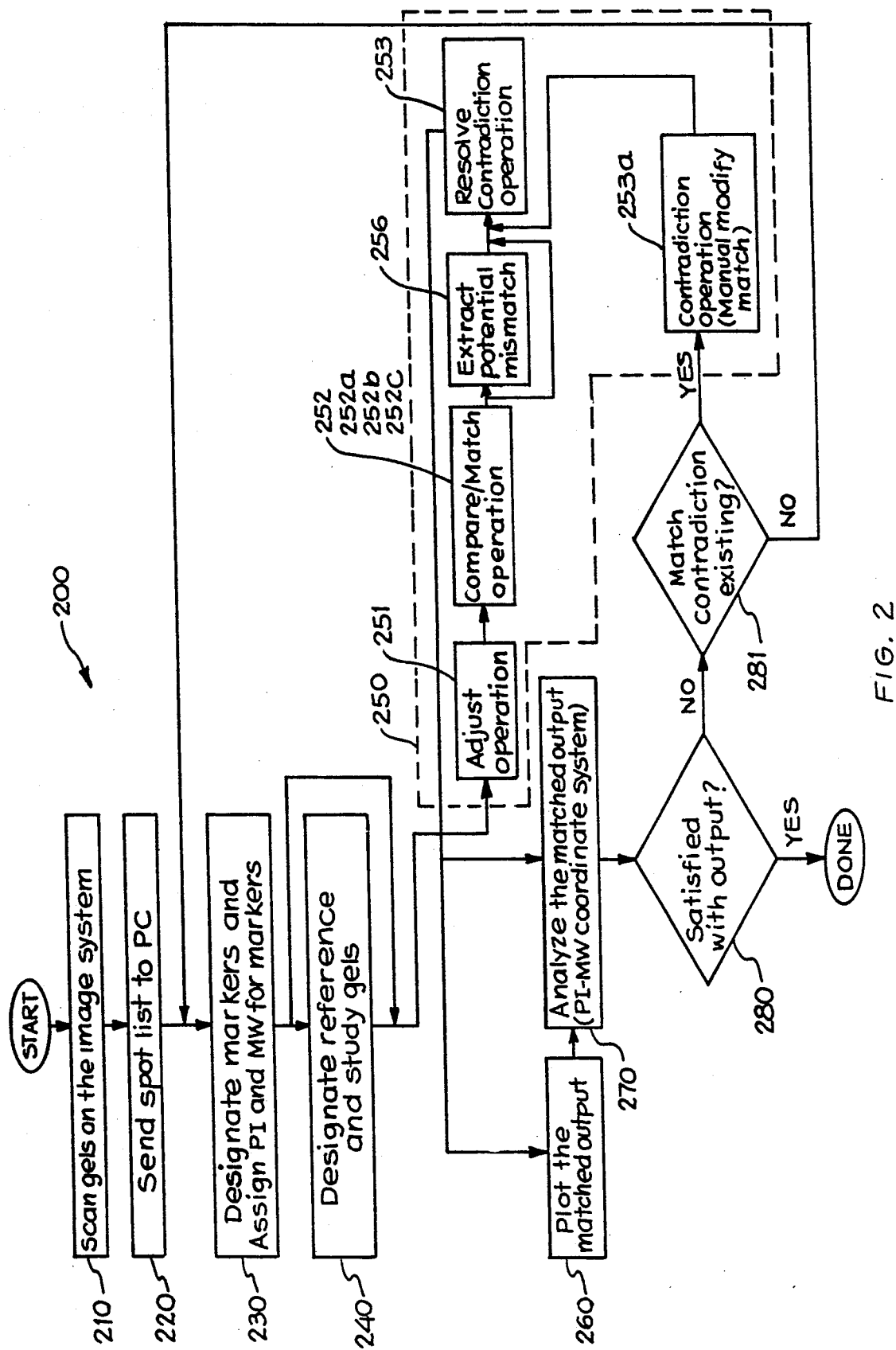
FIG. 2 illustrates a flow chart of the operations of a software program, that implements the present invention.

FIG. 2 illustrates a flow chart summary of the steps involved in performing the 2-D gel matching task in accordance with the present invention. In the preferred embodiment, the steps are performed utilizing a software product 200 that will be commercially available under the trademark "MATCHWARE" from the University of Arizona in Tucson, Ariz. forthwith filing of this patent application. Initially, a gel is scanned to produce gel spot data as indicated in steps 210 and 220. The manner of generating the initial spot data information is not the subject of the present invention, which generation of data includes the use of software programs that are known in the art and are thus not describe herein. The data generated includes the spot's identification, gel name, x-y coordinate values, integrated intensity, spot area, spot height and width. The state of the art being that the spot listing data available from these software programs cannot be used in its raw form to produce accurate and efficient spot comparison and spot matching task due to distortions present in the initial gel preparation. Thus, in accordance with the presence invention, further manipulation of the raw data is undertaken to compensate for the distortions.

Figure 6A:
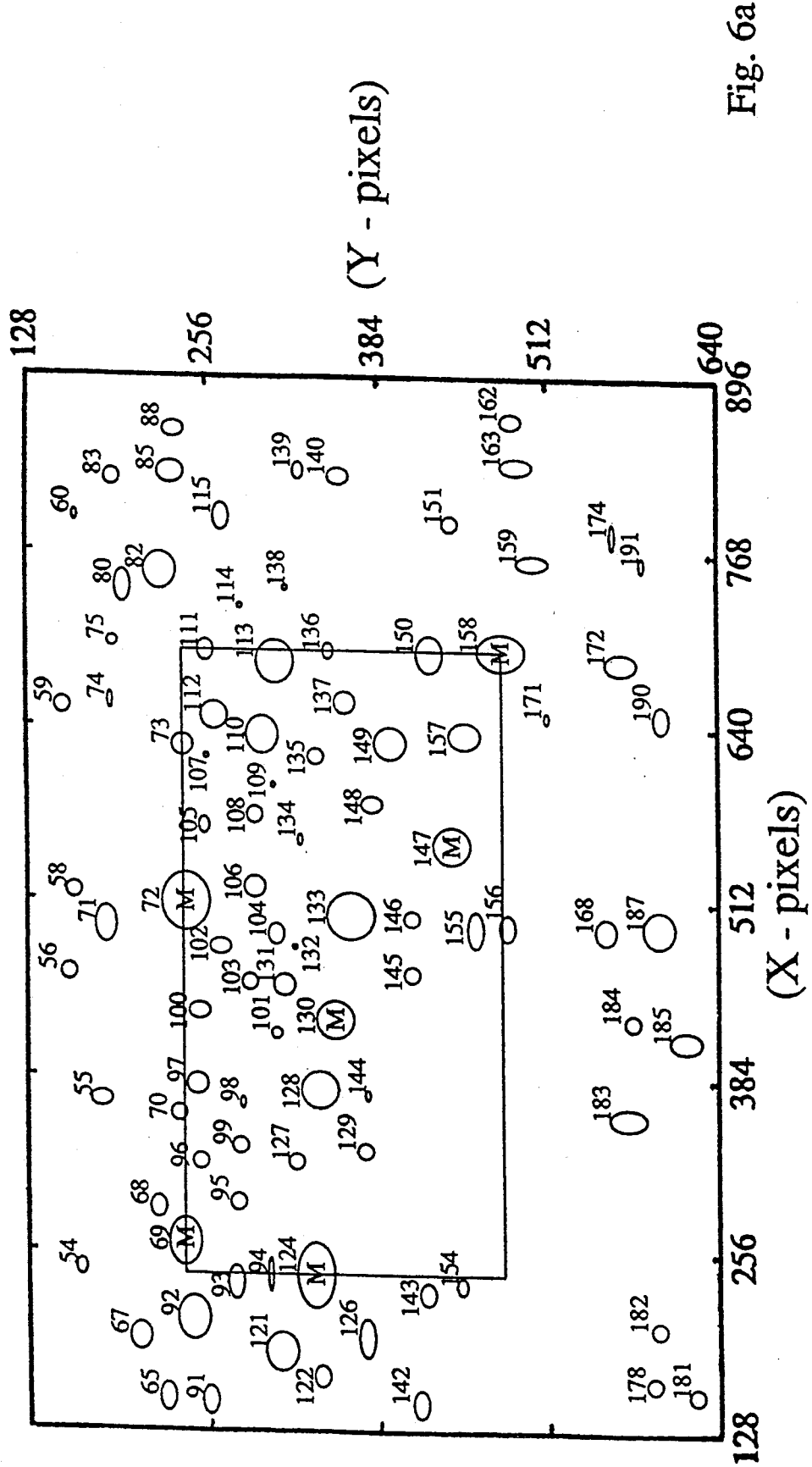
FIG. 6a illustrates selected gel spot images as scanned for gel "a".
Figure 6B:
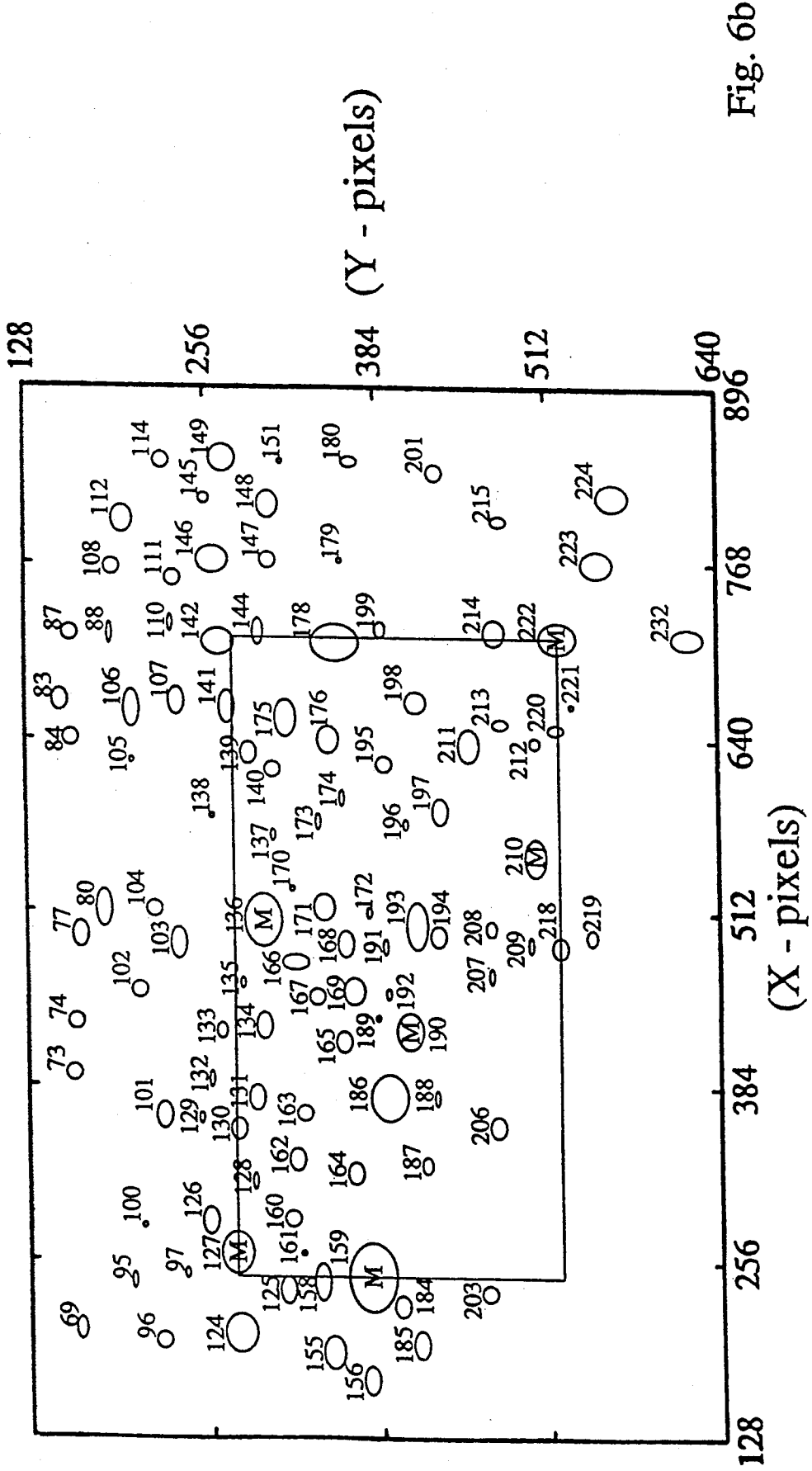
FIG. 6b illustrates selected gel spot images as scanned for gel "b".
Figure 6C:
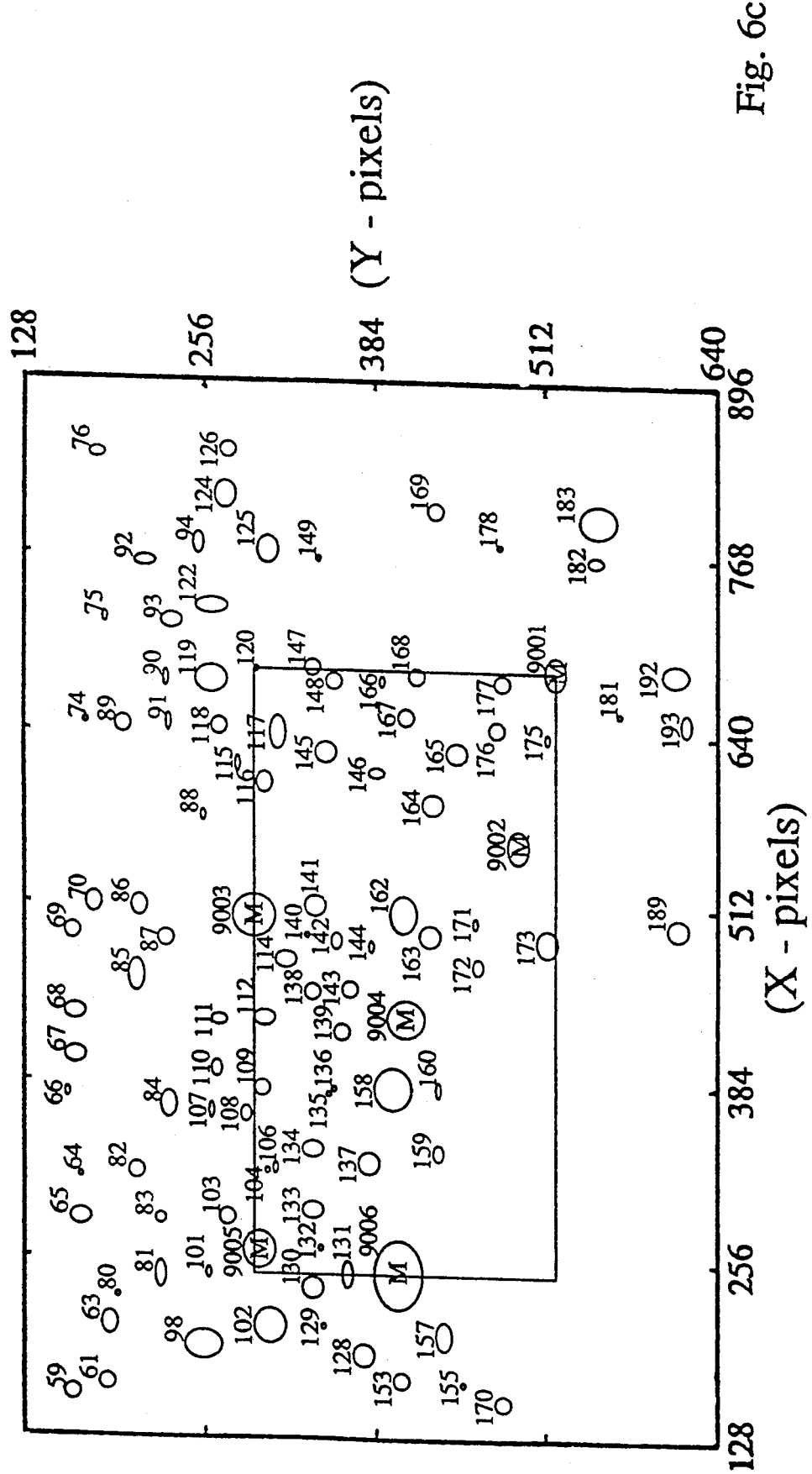
FIG. 6c illustrates selected gel spot images as scanned for gel "c".

The data available at computer 120 is typically a 1024 × 1024 pixel array of the gel images under investigation, see generally FIGS. 6a, 6b and 6c discussed in more detail below. Once the spot data is available at computer 120, and according to the data flow steps 230 and 240 shown in FIG. 2 and further referenced in FIGS. 3 and 4, the user can manipulate the raw data, labeled .1st in FIG. 4 to designate which gel is to be the reference gel and which gel or gels are to be the study gel(s). The user can further manipulate the gel image to investigate a windowed spot pattern with dominant marker spots and all of the unknown numbered reference or study spots, depending upon which gel they are contained, see generally FIGS. 7a, 7b, and 7c discussed in more detail below.

Figure 7A:
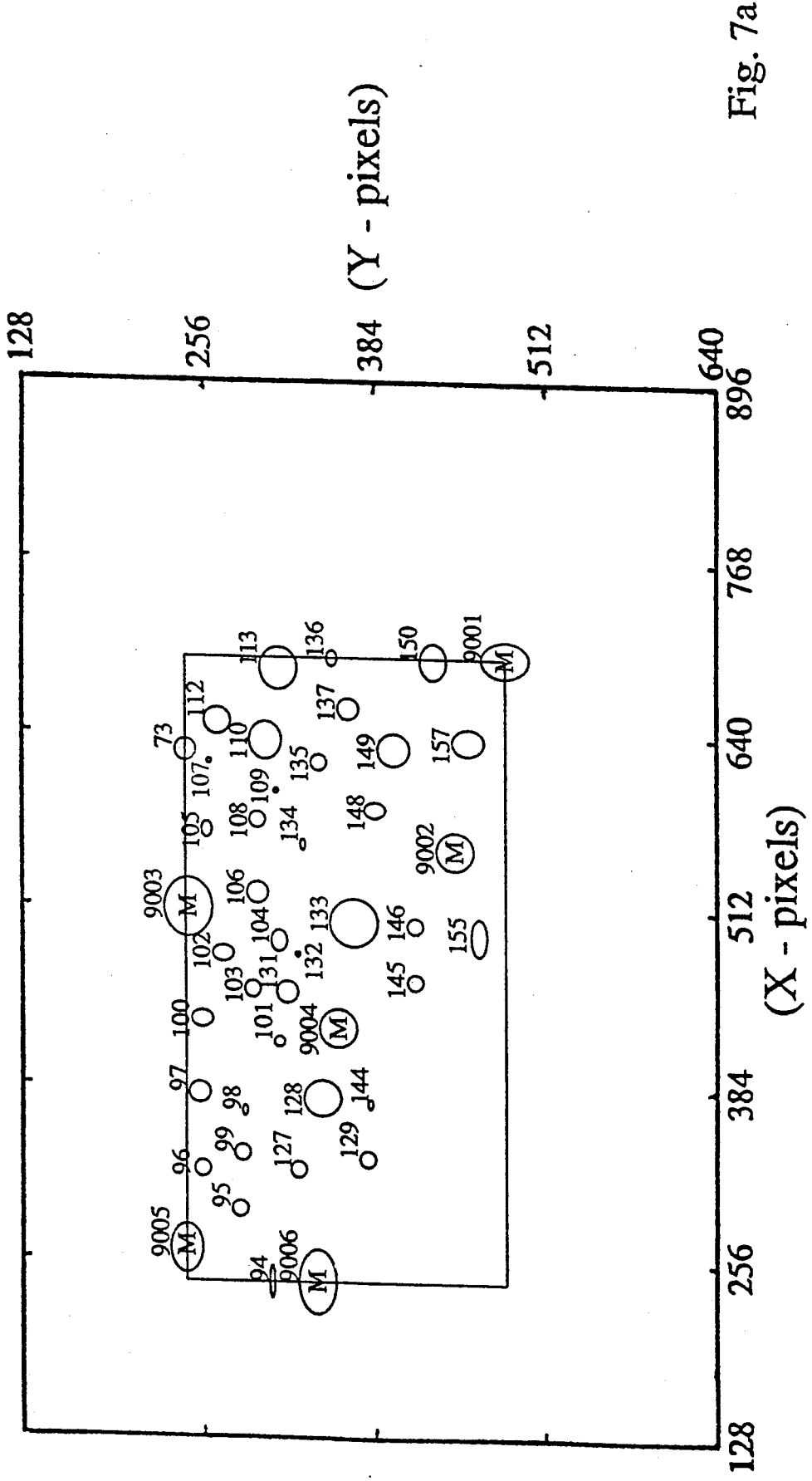
Figure 7B:
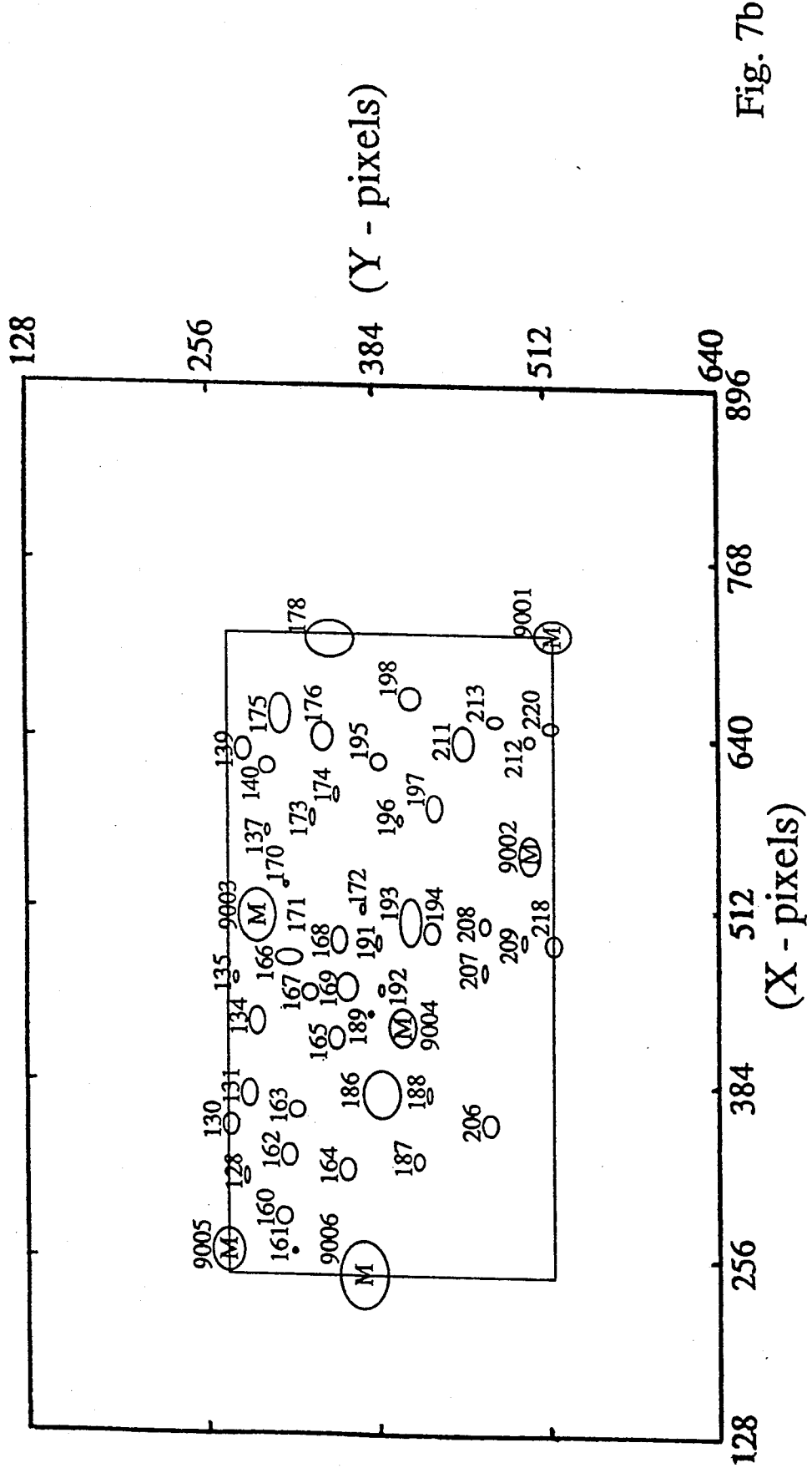
FIG. 7b is a corresponding windowed spot pattern for gel "b" illustrated in FIG. 6b.
Figure 7C:
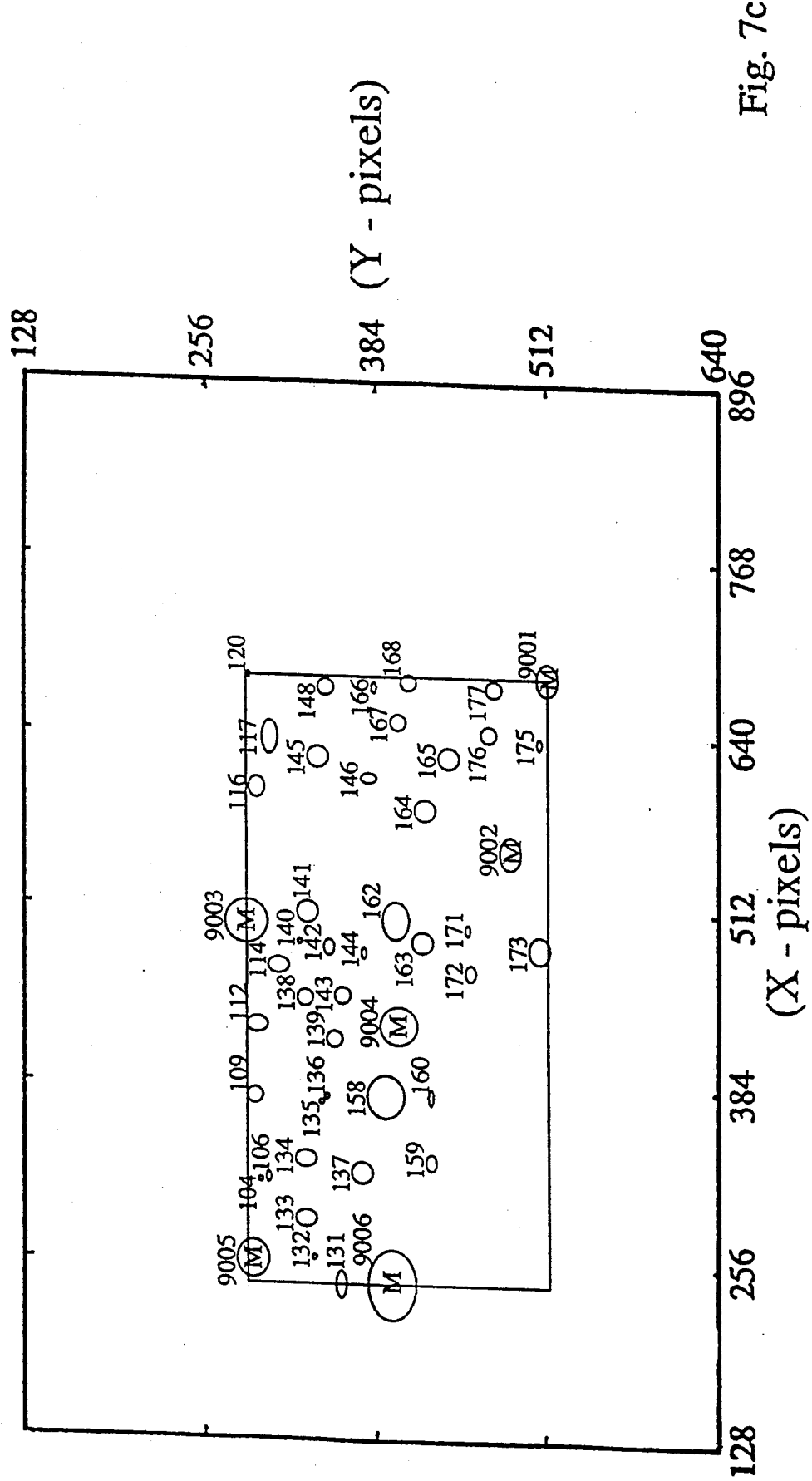
FIG. 7c is a corresponding windowed spot pattern for gel "c" illustrated in FIG. 6c.

By example, reference microfiche Appendix C containing Appendices C1, C2 and C3 provide data for the three gels, labeled "a", "b" and "c", respectively which gels are used herein to aid in understanding the present invention. Microfiche frame labeled Appendix C provides a listing and description of data files generated by "MATCHWARE" during the spot matching task, Appendix C1-(2-6) contains the reference data for the gel labeled "a", used to generate hardcopy of the gel's spot image, which spot images are depicted partially in FIG. 6a and more selectively in FIG. 7a illustrating the windowed spot pattern of interest containing dominant marker spots labeled m. The gel selected as the reference gel is generally determined by the operator as representing the best specimen from the group of gels, i.e. the one with the least visible distortions. Appendices C2-(2-7) and C3-(2-6) contain information about the two other study gels labeled "b" and "c". FIGS. 6b and 6c are partial hardcopy representations of the two study gel's spot images, while FIGS. 7b and 7c illustrate the selected windowed spot patterns of interest containing dominant marker spots, also labeled m. The corresponding spot data listing is contained in appendices C2-(2-7) and C3-(2-6). Collectively, the data is referred to as 210a for the reference gel and 210b and 210c for the two study gels, in FIG. 4. The PI and MW data is also inputted for later use in the analysis as indicated in step 230 in FIG. 4.

Figure 2A:
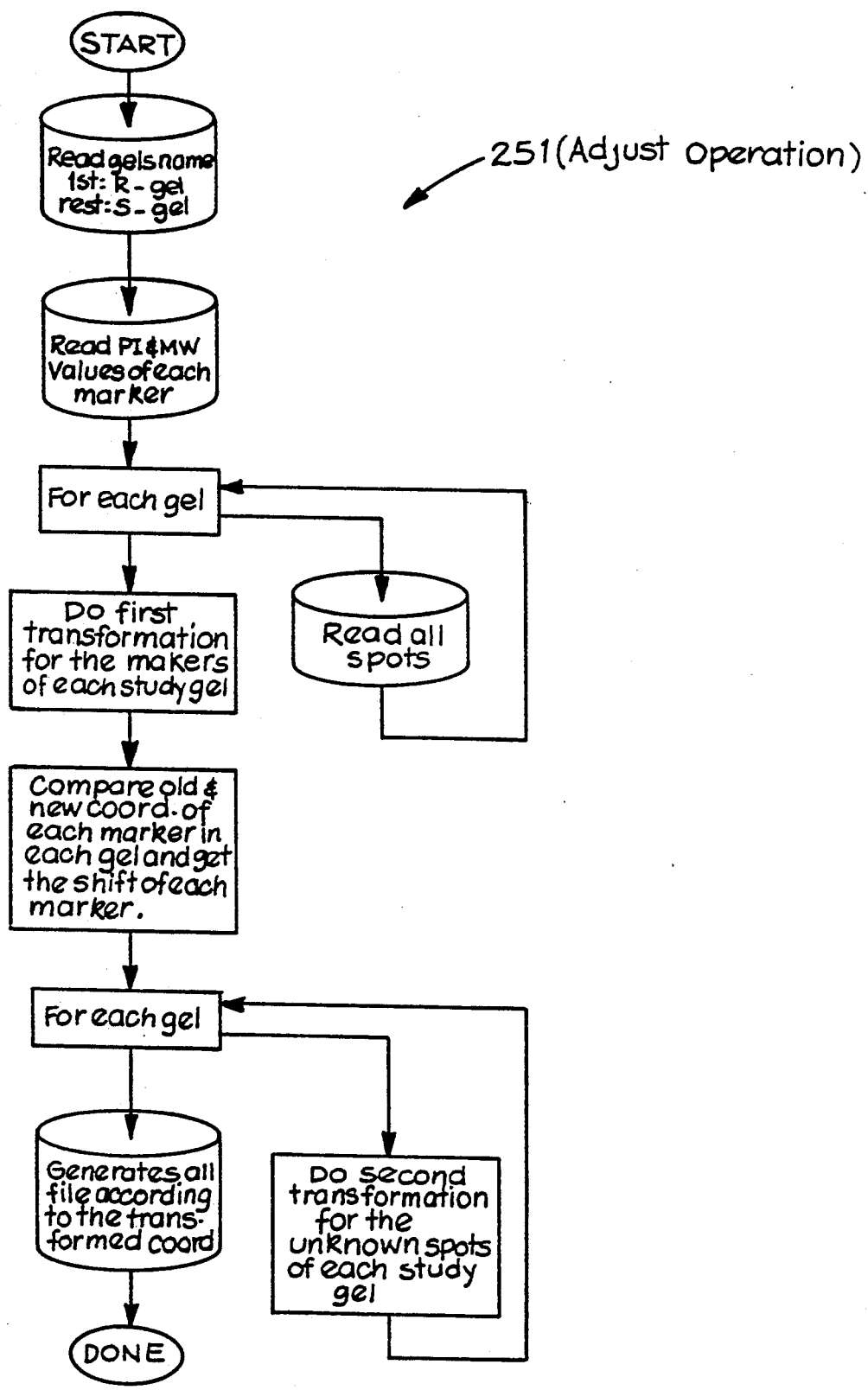
FIG. 2a illustrates a flow chart of the adjust operation portion of the present invention.

Once the gels under investigation are set up for analysis, step 250, as shown in FIG. 2, is executed to selectively perform various subroutines. Included in step 250 is a two-stage spot coordinate transformation step 251 (labeled adjust operation and shown in more detail flow chart in FIG. 2a and in appendices B(1-23) which comprise a source code listing of the adjust subroutine that performs the two-stage spot coordinate transformations), a comparison and match step 252 (shown in more detail in FIGS. 2b, 2c and 2d) based on using multiple or single reference gels and supported by a resolve spot matching contradiction step 253 (shown in more detail in FIG. 2f) and an extract potential mismatched spots step 256 (shown in more detail in FIG. 2e). Appendices A(1-2) provide a brief description of the subroutine steps executed during the adjust operation illustrated in FIG. 2a. Similarly, Appendices A(3-5) provide a brief description of the subroutine steps executed during the compare and match operations illustrated in FIGS. 2b, 2c and 2d. Appendix A6 provides a brief description of the solve cluster operation step executed during the resolve contradiction operation illustrated in FIG. 2f. Appendix A7 provides a brief description of the solve cluster operation step executed during the extract potential mismatch operation illustrated in FIG. 2e.

In the adjust operation 251, the two-stage coordinate transformation includes: (1) performing a first transformation step that transforms positional coordinates of the reference marker spot members and the unknown reference spot members in the reference gel, and each spot marker member in the study gel(s) set from the original scan coordinate system to a new reference coordinate system. This first transformation step results in each member of the set of study marker spots being in a registered relationship with a corresponding spot marker member of the set of reference marker spots. It should be noted that the coordinates of the spot members in reference gel "a" remain the same after the first transformation. (2) performing a second transformation step that transforms positional coordinates of each of the unknown study spot members from the scan coordinate system to the reference coordinate system, the second transformation step comprises: (a) determining an effective range associated with each study marker spot, i.e. the distance associated with an influence which a dominant marker spot has over the surrounding spots which form a spot cluster. The effective range is calculated for each marker spot by locating the nearest marker neighbor to the marker spot and then assigning one-half of the distance between the marker and its nearest neighbor marker to be its effective range, (b) determining an attraction pairing relationship between a particular study marker spot member and a particular unknown study spot member, this attraction pairing relationship being determined by utilizing the effective range of the marker spots by a first rule for finding the nearest and second nearest markers to the unknown study spot, if this unknown study spot is within the effective range of the nearest marker, then the movement value of this unknown study spot into the new reference coordinate system is same as the movement value of the nearest marker spot. A second rule for determining the pairing relationship can be used if the current unknown spot is within the intersection of two times the effective range of the nearest and second nearest marker, then the movement value of this spot is same as the average movement value of the nearest and second nearest marker, otherwise the pairing relationship defaults to the first rule, (c) determining positional coordinates in the reference coordinate system for each unknown study spot member by adjusting the original scan coordinates for each unknown study spot member by a shift amount, or movement values, equivalent to the first transformation shift amounts of the corresponding paired study marker spot member, and (d) repeating the pairing and new coordinate location determining steps for all unknown study spot members in a gel and for all gels being investigated. After the second transformation step, the PI and MW values of the unknown study spot members are determined using interpolation techniques based on PI and MW values previously assigned to the study marker spot members. Adjusted spot datafiles 251a (x.als), 251b (x.mks) and 251c (x.att) are produced as a result of the foregoing two-stage transformation and also include results of the PI and MW interpolation steps. As noted above, FIG. 7a represents a hardcopy printout of the windowed spot pattern whose data is listed in Appendices C4(2-4) obtained from corresponding spot datafiles 251a (a.als), 251b (a.mks) and 251 c (a.att) shown in FIG. 4 for the reference gel that was manipulated by the 251 adjust operation, see Appendix C for file descriptors. Also as noted above, FIGS. 7b and 7c are representations of hardcopy printout of the windowed spot patterns for the two study gels "b" and "c". Appendices C5(2-6) and C6(2-4) are the computer program data listing obtained from corresponding spot datafiles 251a (b.als, c.als), 251b (b.mks, c.mks) and 251c (b.att, c.att), respectively, resulting from manipulating these gels through the two-stage spot coordinate transformation.

Figures 2B, 2C:
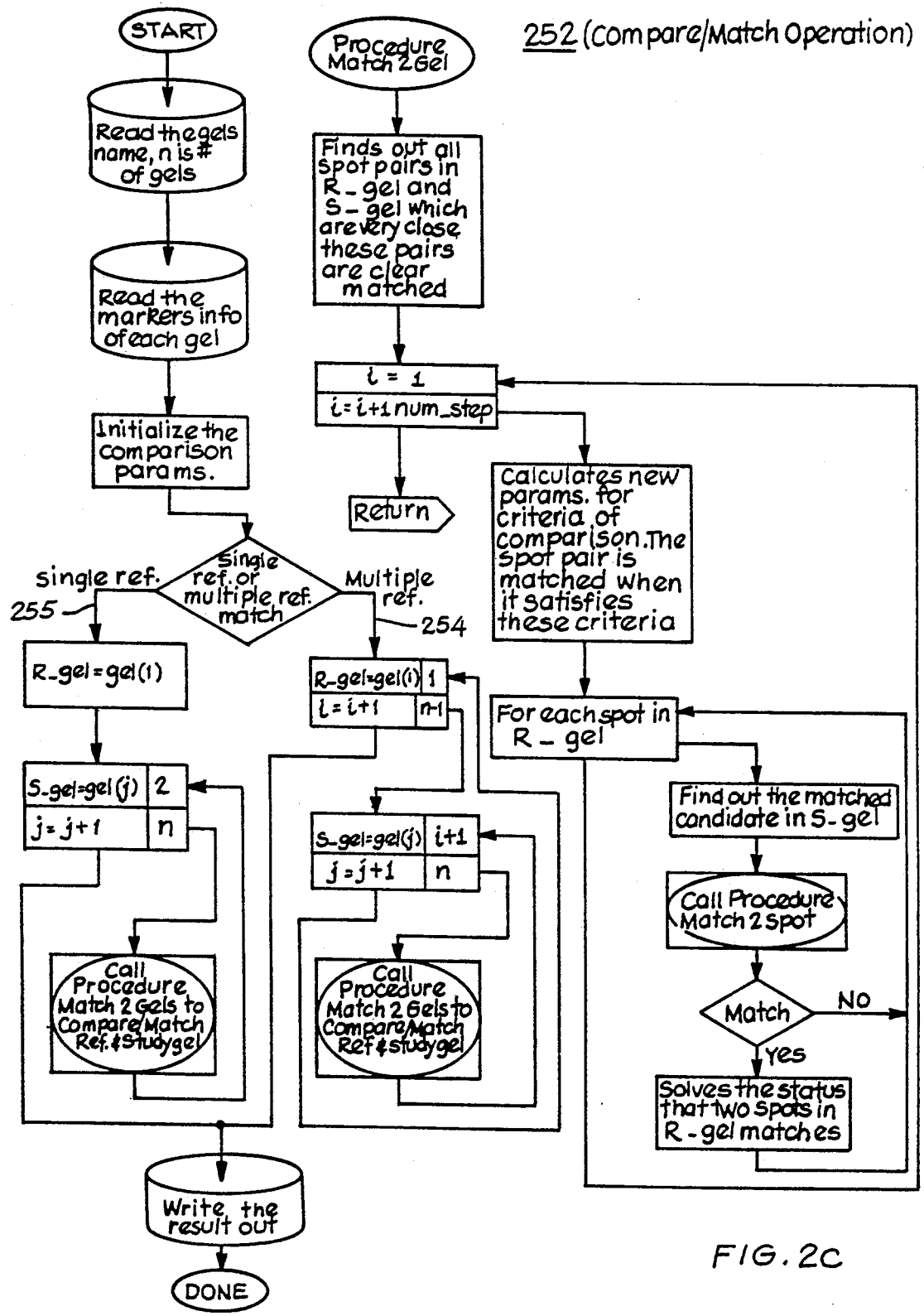
FIGS. 2b, 2c and 2d illustrate a set of flow charts of the compare and match operation portion of the present invention, that are used to determine potentially matching pairs of spots.
Figures 2D, 2E:
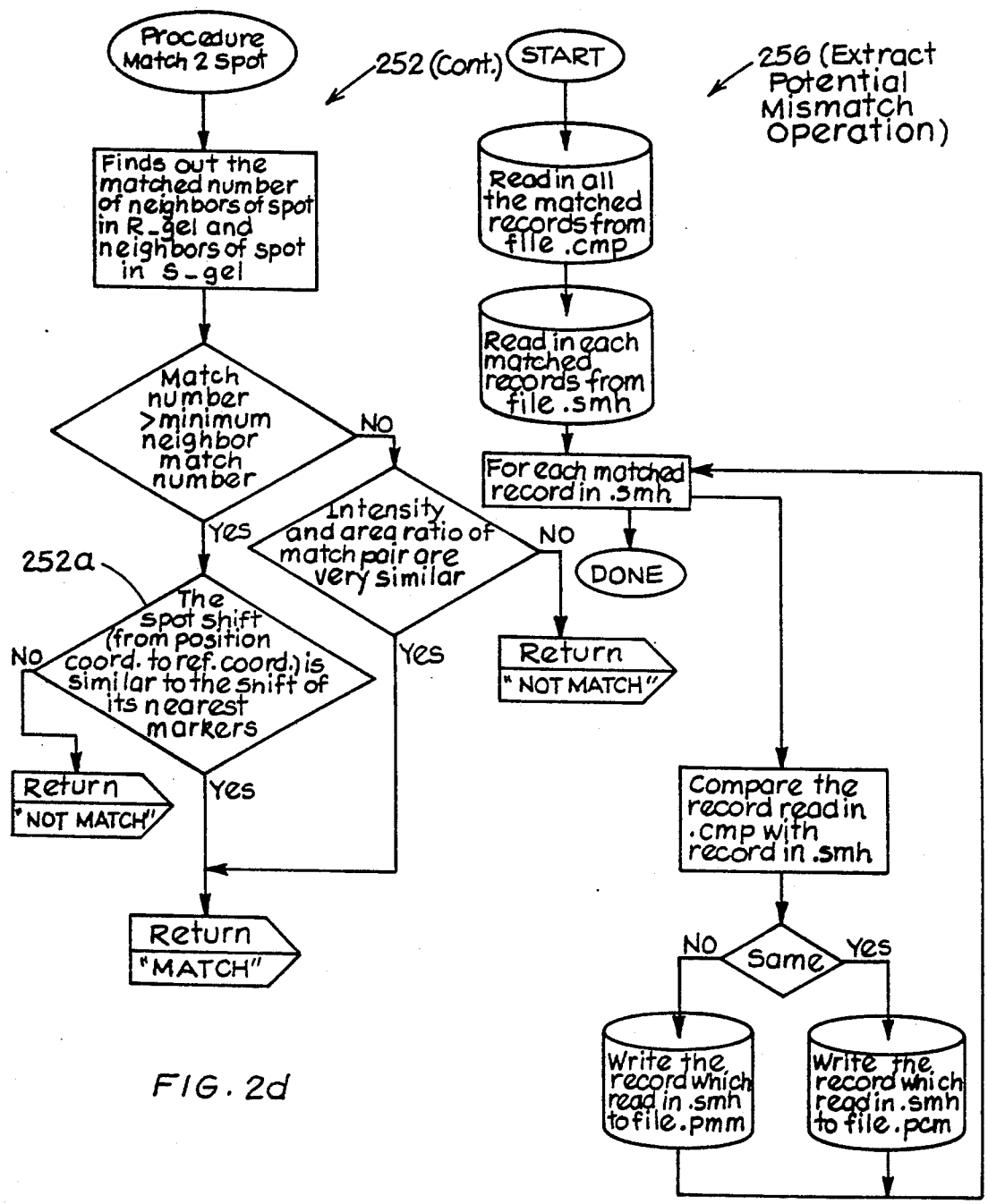
FIG. 2e illustrates a flow chart of the extract potential mismatch operation portion of the present invention, that compares the matching results with a file that contains matching results that are considered more likely to be correct.
Figure 2F:
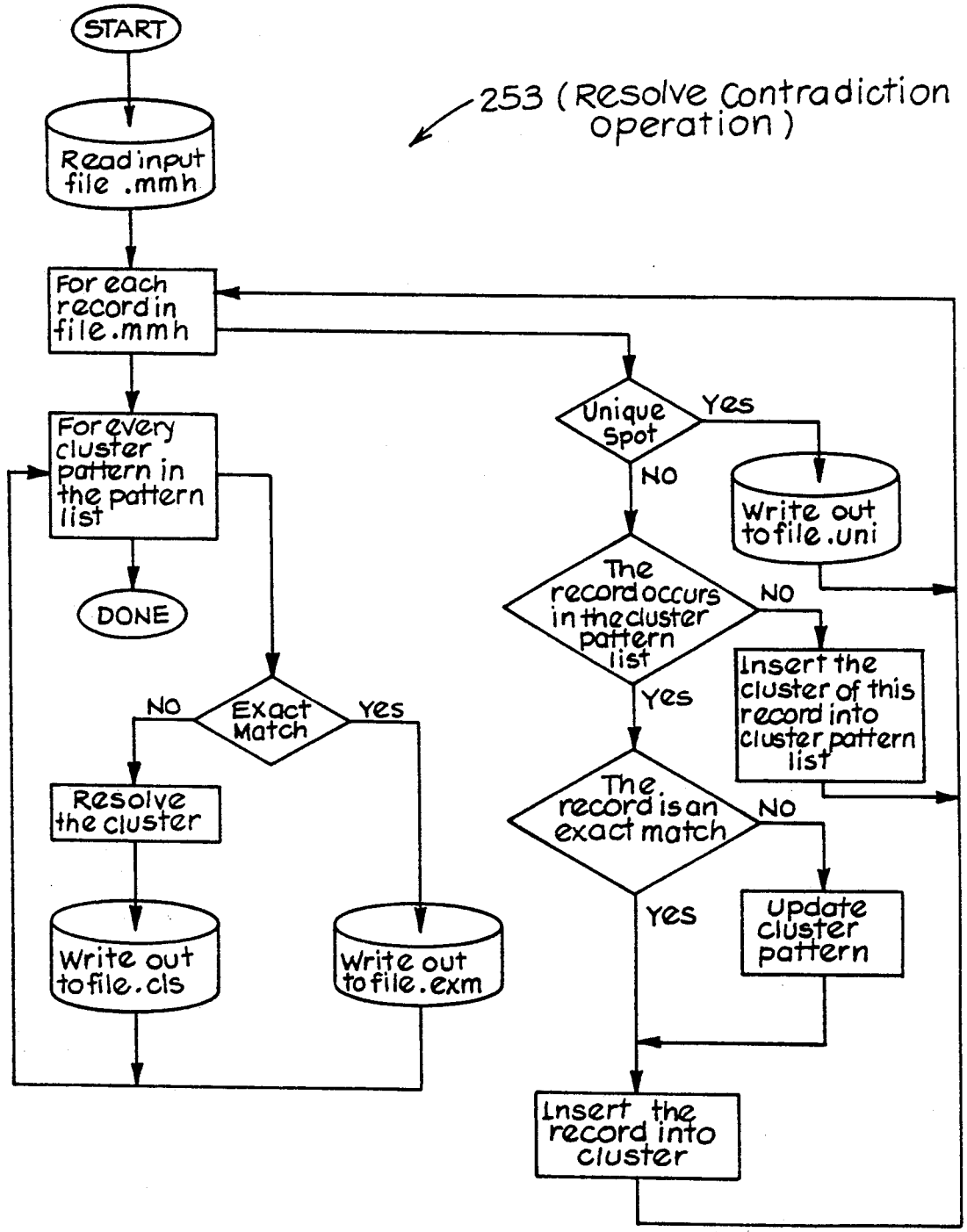
FIG. 2f illustrates a flow chart of the resolve contradictions operation portion of the present invention that eliminates ambiguous matching results.

At this point in the analysis, all the necessary data to perform the comparing and matching tasks, denoted in FIG. 2 as operation 252 and depicted in the flow charts of FIGS. 2b, 2c and 2d, is available. The comparing task primarily involves taking every identified unknown spot in each of the gels and analyzing the recorded data, using as required, the spot's old and new x-y coordinate values, integrated intensity, spot area, PI and MW data, spot height and width for comparing against similar data of the other unknown spots and grouping the results as sets of potential matching spots. In the cases involving more than two study gels, the user has an option to either conduct a matching exercise based on using a single designated reference gel and comparing other study gels against and hence following the data flow using block 255 shown in FIG. 4 and in the flow chart of FIG. 2b, or conducting a matching exercise iteratively designating every gel as a reference gel, i.e. multiple reference gels and following the data flow using block 254, also as shown in FIG. 4 and in the flow chart of FIG. 2b.

Figure 5:
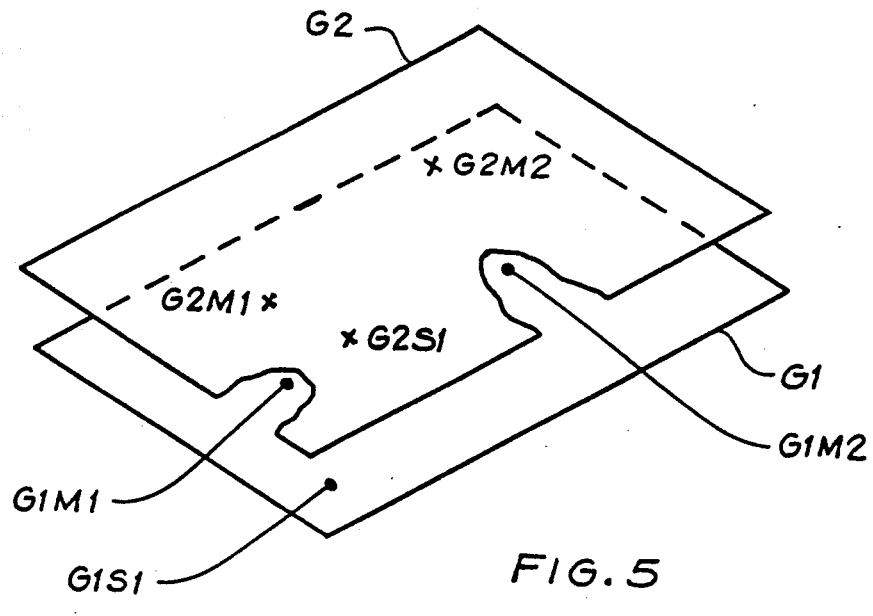
FIG. 5 illustrates a pair of gels in an overlay relationship to aid in understanding a vector analysis performed by the second transformation stage of present invention.
Figure 5A:
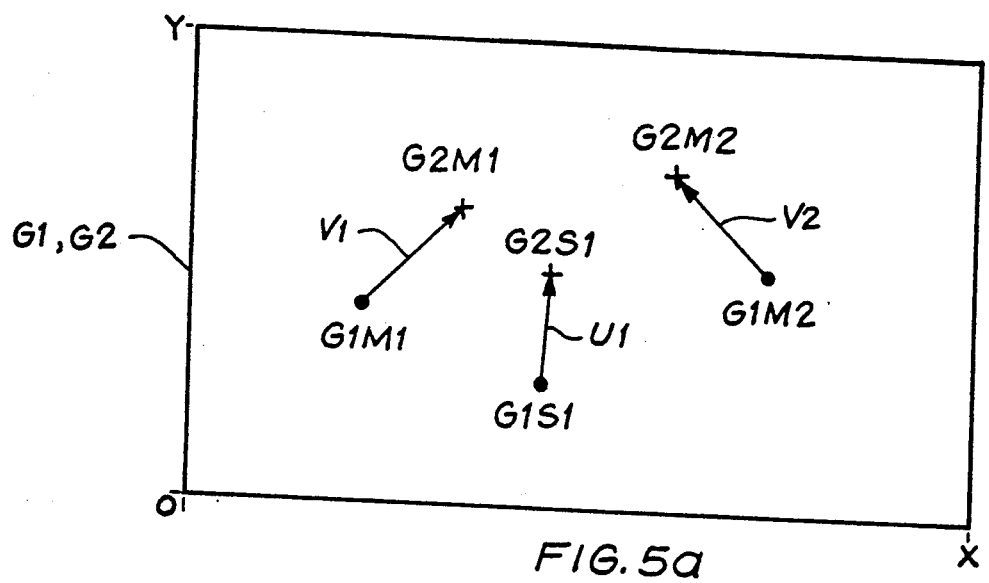
FIG. 5a illustrates a planer vector diagram based on the graphical gel overlay depicted in FIG. 5. illustrating a study spot's nearest marker spot and the next nearest marker spot.
Figure 5B:
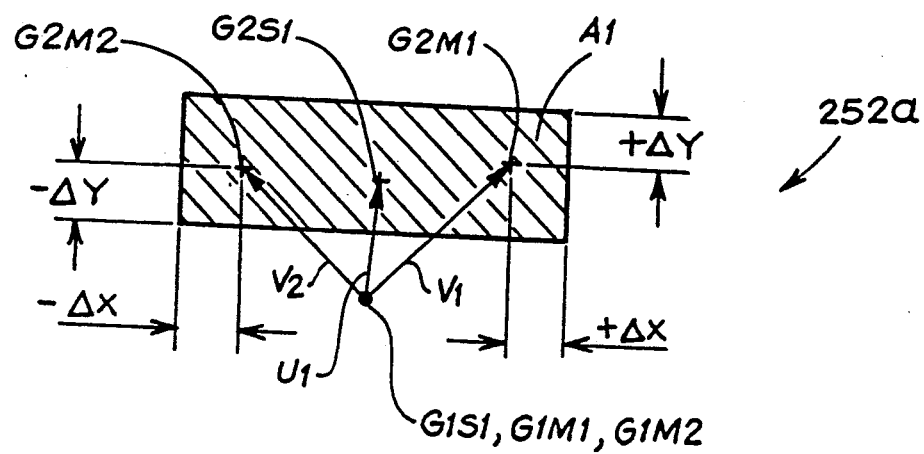
FIG. 5b is a diagram illustrating an accpetable rectangular area for exact matching spots constructed by using the x and y components of vectors depicted in FIG. 5a shifted and having a common origin.

Before a matched spots outcome is reported, i.e. based on exact matching coordinates, spot size or intensity, the present invention also performs a verification step 252a on the set of potentially matching spots, regardless of whether conducting a matching exercise according to operation step 254 or 255. The verification inquiry is part of the query depicted in the flow chart of FIG. 2d. Verification step 252a utilizes the potentially matching spot's nearest and next nearest marker spots, and their original positional data, to construct a pair of marker spot vectors for juxtaposition comparison with an unknown spot's vector formed by joining a first and second one of the potential matching unknown spots in two gels, also using the unknown spot's original positional data. FIG. 5 shows gel G1 and G2 in an overlay relationship where a first unknown spot G1S1, having nearest marker spot G1M1 and second nearest marker spot G1M2, supposedly matching second unknown spot G2S1, having nearest marker spot G2M1 and second nearest marker spot G2M2. The pair of marker spot vectors comprise a first vector V1 formed by graphically joining G1M1 to G2M1 and a second vector V2 formed by graphically joining G1M2 to G2M2, while the unknown spot's vector U1 is formed by graphically joining G1S1 to G2S1, see FIG. 5a. To maintain consistency in the vector's direction, one of the gels should be designated as containing spots that form the tail of the vector and the other as containing spots that form the head of the vectors. The juxtaposition comparison requires shifting the three vectors such that their tails are on a common point to establish whether the head of the unknown spot's vector U1 falls within an acceptable rectangular area A1 formed by minimum and maximum x and y limits, see FIG. 5b for construction of the acceptable rectangular area A1, and vector U1's head falling within area A1 indicating that unknown spots G1S1 and G2S1 are a matching pair. The size of the acceptable rectangular area is based on x and y components of the head of vectors V1 and V2. The vertical boundaries are extended away from the actual x values for the V1 and V2 heads, while the upper y boundary is extended upward from the y value of the V2 vector and the lower boundary is extended downward from the y value of the V1 vector. The x and y amounts extended are user adjustable tolerance amounts, typically 0.5 milli-meters. If the head of vector U1 does not fall within the area A1, a no match situation exists for the particular pair of unknown spots, whose vector is being manipulated.

Figure 3:
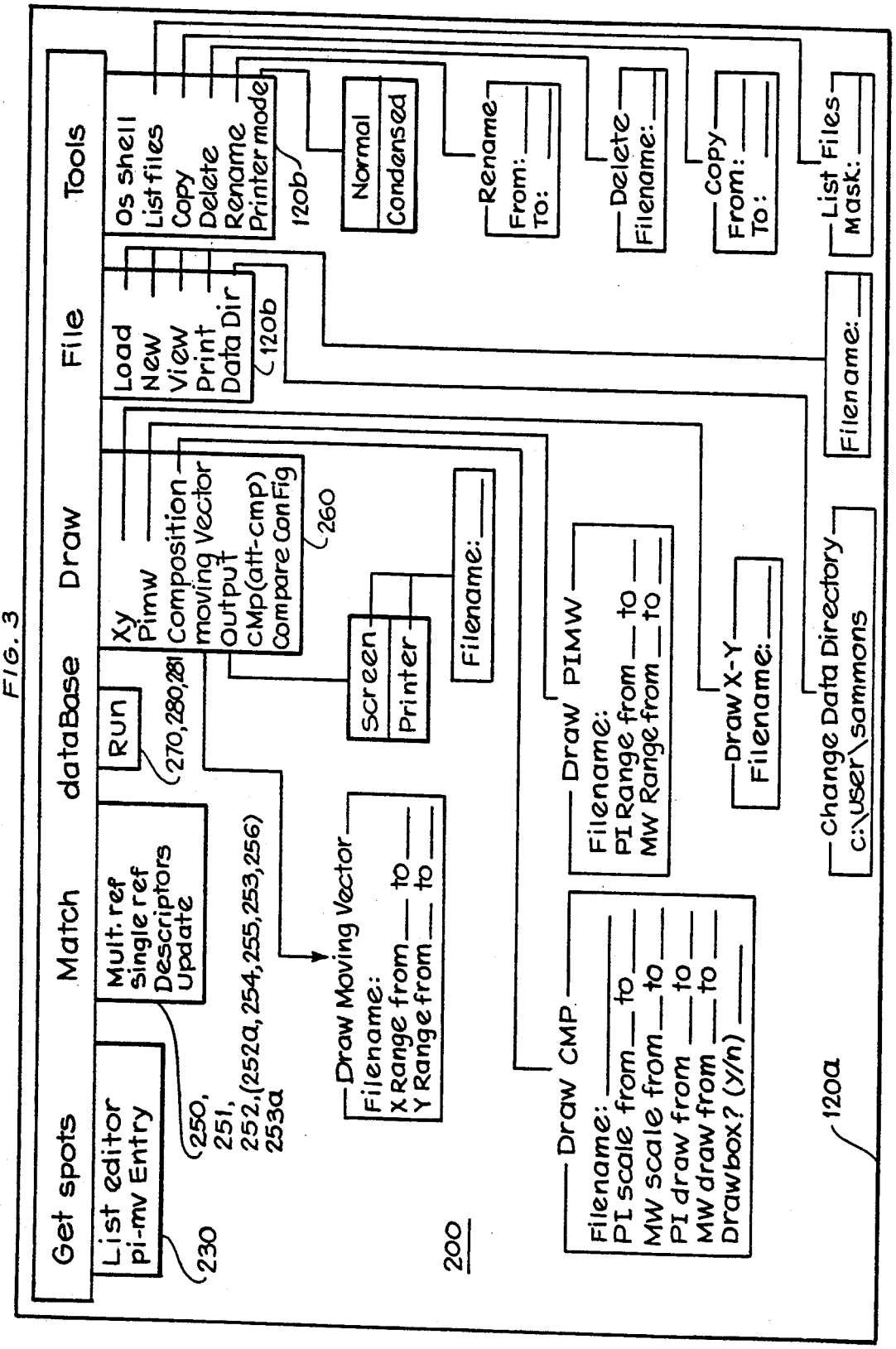
FIG. 3 illustrates a block diagram overview of a computer monitor screen illustrating a menu of the interactive computer software program, termed "MATCHWARE", that implements the present invention.
Figure 4:
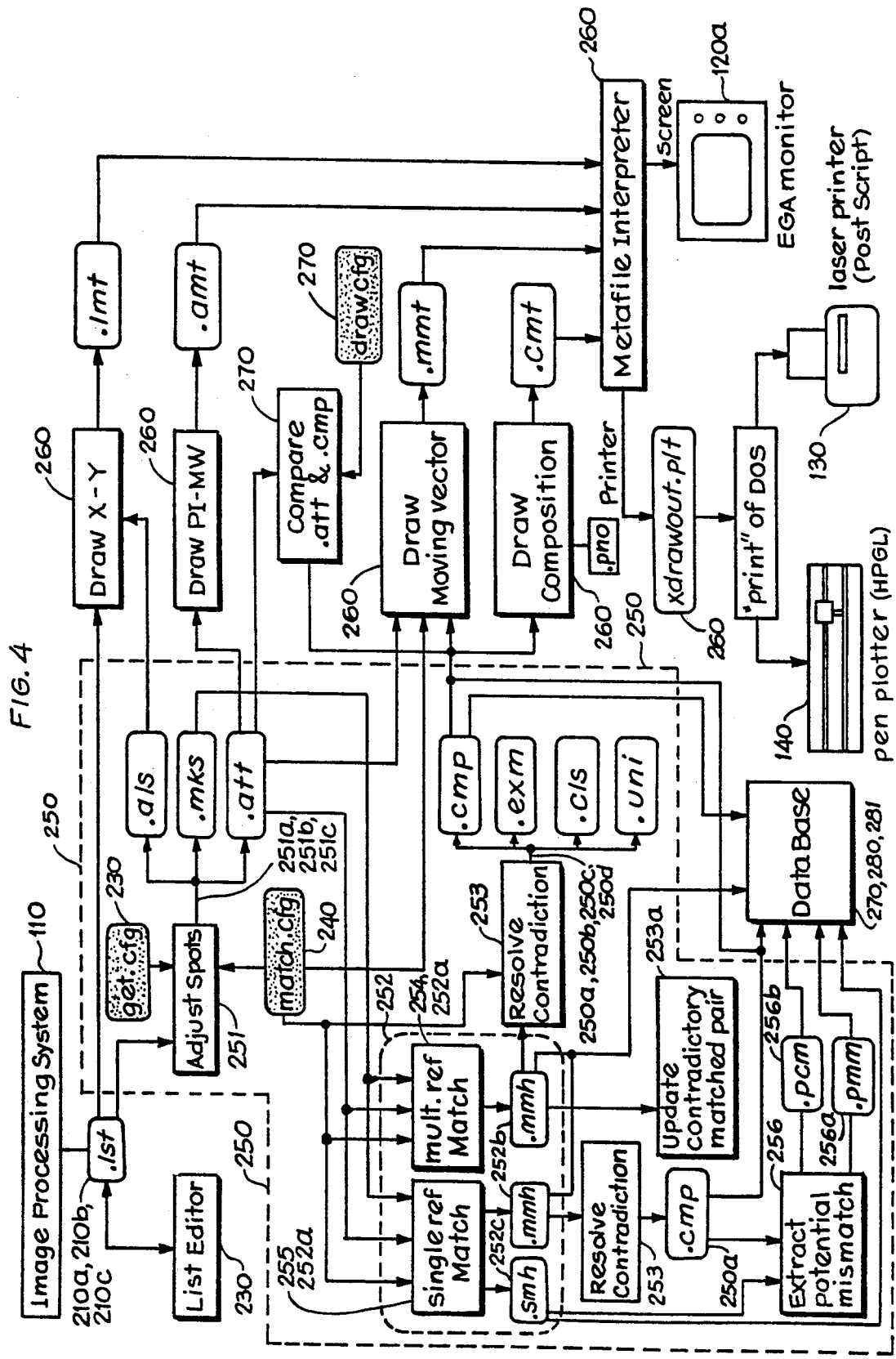
FIG. 4 is a detailed data flow chart of the operation of "MATCHWARE" software program that implements the present invention.

Assuming that a user wishes to manipulate the gel spot data based on multiple reference gel analysis, i.e. operation step 254, then the data flow depicted in FIG. 4 would result, see also FIG. 3 for subroutine options available. Following the data flow shown in FIG. 4 using operation step 254, the present invention addresses ambiguous situations in reported spot matching results (data file .mmh shown as 252b in FIG. 4) by processing the affected unknown spots through the resolve contradiction subroutine 253, as shown in FIG. 4 and also as shown in the flow chart in FIG. 2f. Appendices D1(1-3), D2, D3, D4(1-3), and D5(1-2) are gel group spot data manipulation results in accordance with the present invention wherein: Appendix D1 is a listing of datafile 252b (abc.mmh) based on multiple reference gels, i.e. results based on each gel being used as a reference in the comparison task and includes matched and unmatched spots before resolving any contradictions contained in the data for the three gels under investigation. Appendix D2 is a listing of datafile 250c of a spot cluster exhibiting contradicting matching results which were extracted from datafile 252b and resolved by resolve contradiction subroutine 253, i.e. a spot(s) that is (are) found matching other spots that logically cannot be explained, for example one spot in one gel matched two spots and these two spots are in the same gel, (datafile 250c is an empty file upon resolving all contradictory clusters). Appendix D3 is a listing of datafile 250d of unmatched spots (termed "unique") as found in the three gels under investigation. Appendix D4(1-3) is a listing of datafile 250b of exact matched spots as determined by the present invention. Appendix D5(2-2) is a composite listing of datafile 250a of a pseudo gel, each member of the composite listing representing a matrix of matching spots having a plurality of rows, each row being identical to the corresponding member in the composite listing. In the 250a listing, negative record label represents matching spots, (two matching spots or three matching spots), while positive record label represents unmatched spots, as found in the three gels under investigation.

Referring now to FIGS. 3 and 4, Appendix E1, is a listing of datafile 252c (abc.smh) similar to datafile 252b except generated using a designated single gel as a reference. Appendix E1 is generated by operation step 255 that is based on using a designated single gel as a reference gel and comparing it against each of the other study gels before generating the results. Datafile 252c has the characteristic that matched and unmatched spots are reported without any matching contradictions which normally results when the matching is based on a multiplicity of reference gels. It has been observed that some of the matching spots results include mis-matched spot data and has led to reporting more matched spots in matching results listings, such as in Appendix E1, than actually exist. Faced with this potential error in matching results using a single gel as a reference gel, the user has the option of further manipulating the data using step 256 to extract potential mismatching spots to improve the accuracy of the match listings, see FIG. 4 and also the flow chart depicted in FIG. 2e. Step 256 allows the user to compare the datafile 252c against a composite datafile 250a, see Appendix D5(1-2), abc.cmp, (generated in background during operation of step 255 and contains the same data as if generated by operation 254, 253), which datafile abc.cmp contains matching results that are considered more likely to be correct. Comparison step 256 then generates potentially mis-matched spots datafile 256a, see Appendix E2, abc.pmm, and a potentially correctly matched spot datafile 256b, see Appendix E3, abc.pcm. In generating datafile 256a and 256b, it is noted that in comparing datafiles 252c against 250a that any potentially correct matching set of spots would be found in both datafile 250a and in 252c, while any potential mis-matched set of spots would be found only in datafile 252c, but not in 250a. Further, after step 256, it is noted that any potentially correct matching set of spots would be mostly found in datafile 256b and least in 256a, while any potential mis-matched set of spots would be found mostly in datafile 256a and least in 256b. Composite datafile 250a is given greater credibility because the matched set of spots found in datafile 250a are determined firstly as a matrix of matching spots using each gel as a reference gel and then repeated according to the number of gels under study. Having processed spot data through operation step 255, the user can then utilize datafile 256a containing the list of potentially mismatched sets of spots as a means of determining whether a particular set of matching spots being examined are part of the potentially mis-matched group of spot and thereby gain a higher confidence level about reported matching results, i.e. the matching results found in datafile 256b or 250b. The spot matching result listed in datafile 256b have an improved accuracy over those listed in datafile 252c in that the potential mismatching spots have been sorted into datafile 256a.

Referring back to FIG. 2, the results from operation 250 may be reviewed in a variety of plotting options 260, see also FIGS. 3 and 4, and may be repeatedly performed after analysis step 270 until a user has thoroughly understood the matching results, which step 270 takes advantage of having the PI and MW data to reinforce matching results based on comparisons in the new x and y coordinate system, and may be repeated using the data base information and may be based on inquiry 280, 281 that considers whether any further contradiction 253a exists, or whether new markers need to be considered, such as by looping back through marker designation step 230 and bypassing step 240.

Therefore, while the present invention has been shown and described herein in what is believed to be the most practical and preferred embodiments, it is recognized that departures can be made therefore within the scope of the invention, which is therefore not to be limited to the details disclosed therein but is to be accorded the full scope of the claims so as to embrace any and all equivalent methods.

We claim:

1. A method of matching two-dimensional (2-D) patterns, said method comprising the steps of:
   (a) image scanning a plurality of 2-D patterns and producing corresponding data files for each scanned 2-D pattern and recording logistic data and pattern physical characteristics data in a scan coordinate system;
   (b) identifying pattern members in each of said scanned 2-D pattern that bound investigative patterns and designating said identified pattern members as marker members;
   (c) designating one of said plurality of 2-D pattern as a reference 2-D pattern, said reference 2-D pattern having a reference pattern member data file which includes a set of reference marker members and unknown reference pattern members each having respective coordinates in said scan coordinate system;
   (d) designating at least one of remaining ones of said plurality of 2-D patterns as a study 2-D pattern, said study 2-D pattern having a study pattern data file which includes a set of study marker members and unknown study pattern members each having respective coordinates in said scan coordinate system;
   (e) performing a first transformation step that transforms positional coordinates of said set of reference marker members, said unknown reference pattern members and each member of said set of study marker pattern members, from said scan coordinate system to a reference coordinate system, said first transformation step resulting in each member of said set of study marker members being in a registered relationship with a corresponding member of said set of reference marker members;
   (f) performing a second transformation step that transforms positional coordinates of each of said unknown study pattern members from said scan coordinate system to said reference coordinate system and generating at least one adjusted data file containing new coordinate information for all pattern members manipulated by said first and second transformation steps;

(g) repeating said steps (d), (e) and (f) on any remaining one of said plurality of 2-D pattern; and (h) comparing coordinates of all pattern members in said at least one adjusted data file and producing results identifying matching pattern members.

2. A method of matching two-dimensional (2-D) patterns, as recited in claim 1, wherein said step (h) further includes the steps of:

verifying that potentially matching unknown spots are within an acceptable vector area formed by marker spot vectors before producing said matching results; and resolving matching results having contradictory matching information among spot pattern members.

3. A method of matching two-dimensional (2-D) patterns, as recited in claim 1, wherein:

said 2-D patterns being protein spot patterns in a plurality of two-dimensional gel electrophoretograms (2-D gels) and said step of identifying said pattern members as marker members further includes assigning isoelectric focusing (PI), and molecular weight (MW) dimensional separation values to said marker members; and said method further includes after performing said second transformation step, interpolating said assigned PI and MW separation values to said marker members to determine PI and MW values for said unknown study patterns.

4. A method of matching two-dimensional (2-D) patterns, as recited in claim 3, wherein:

said step of comparing includes the step of verifying that potentially matching unknown spots are within an acceptable vector area formed by marker spot vectors before producing said matching results;

said method further includes the step of analyzing said matching results using PI and MW separation values resulting from said interpolating step; and resolving matching results having contradictory matching information among pattern members.

5. A method of matching two-dimensional (2-D) patterns, as recited in claim 3, wherein after said step of comparing and producing matching results includes:

analyzing said matching results using PI and MW separation values resulting from said interpolating step; and repeating said steps (b) through (h) and said analyzing step.

6. A method of matching protein spot patterns in a plurality of two-dimensional gel electrophoretograms (2-D gels), said method comprising the steps of:

(a) image scanning each of said plurality of 2-D gels and producing corresponding spot data files for each 2-D gel that contain logistic data and spot physical characteristics data in a scan coordinate system;

(b) identifying spot members in each of said plurality of 2-D gels that bound investigative spot patterns and designating said identified spot members as marker spot members;

(c) designating one of said plurality of 2-D gels as a reference 2-D gel, said reference 2-D gel having an associated reference spot data file including a set of reference marker spot members and unknown reference spot members having respective coordinates in said scan coordinate system;

(d) designating at least one of remaining ones of said plurality of 2-D gels as a study 2-D gel, said study 2-D gel having an associated study spot data file including a set of study marker spot members and unknown study spot members having respective coordinates in said scan coordinate system;

(e) performing a first transformation step that transforms positional coordinates of said set of reference marker spot members, said unknown reference spot members and each member of said set of study marker spot members from said scan coordinate system to a reference coordinate system, said first transformation step resulting in each member of said set of study marker spot members being in a registered relationship with a corresponding member of said set of reference marker spot members;

(f) performing a second transformation step that transforms positional coordinates of each of said unknown study spot members from said scan coordinate system to said reference coordinate system and generating at least one adjusted data file containing new coordinate information for all spot pattern members manipulated by said first and second transformation steps;

(g) repeating said steps (d), (e) and (f) on any remaining one of said plurality of 2-D gels; and (h) comparing coordinates of all spot pattern members in said at least one adjusted data file and producing results identifying matching spot pattern members.

7. A method of matching protein spot patterns in a plurality of two-dimensional gel electrophoretograms, as recited in claim 6, wherein said step of performing a second transformation step comprises:

(i) determining an effective range associated with each study marker spot member of said set of study marker spot members, (ii) determining an attraction pairing relationship between a particular study marker spot member and a particular unknown study spot member, said attraction pairing relationship being determined utilizing said effective range as determined for said particular study marker spot member, (iii) determining positional coordinates in said reference coordinate system of said particular unknown study spot member by adjusting original scan coordinates by shift amounts equivalent to transformation shift amounts of said particular study marker spot member that resulted from said first transformation step, and (iv) repeating said (ii) and (iii) steps for all unknown study spot members.

8. A method of matching protein spot patterns in a plurality of two-dimensional gel electrophoretograms, as recited in claim 6, wherein:

said step of identifying said spot members as marker spot members further includes assigning isoelectric focusing (PI), and molecular weight (MW) dimensional separation values to said marker spot members; and said method further including, after performing said second transformation step, interpolating said assigned PI and MW separation values to said marker spot members to determine PI and MW values for said unknown study patterns.

9. A method of matching protein spot patterns in a plurality of two-dimensional gel electrophoretograms, as recited in claim 8, wherein:
   said step of comparing includes the step of verifying that potentially matching unknown spots are within an acceptable vector area formed by marker spot vectors before producing said matching results; and
   said producing matching results includes generating a matched and unmatched spot datafiles for said unknown study spot members.

10. A method of matching protein spot patterns in a plurality of two-dimensional gel electrophoretograms, as recited in claim 9, wherein:
   said producing matching results further includes generating a cluster datafile having contradictory matching information about certain ones of said unknown study spot members that match certain other ones of said unknown spot members in a contradictory manner; and
   said method further includes resolving said contradictory matching information, producing spot matching results void of said contradictory matching information and updating matching results as required to improve accuracy and efficiency of the matching task.

11. A method of matching protein spot patterns in a plurality of two-dimensional gel electrophoretograms, as recited in claim 10, wherein:
   said unmatched spot datafile comprises a unique datafile having said unknown study spot members with coordinates that do not match with any other spot members.

12. A method of matching protein spot patterns in a plurality of two-dimensional gel electrophoretograms, as recited in claim 10, wherein:
   said verification step includes a juxtaposition comparison that involves moving a constructed unknown spot's vector formed from a pair of said potentially matching unknown spots toward a pair of marker spot's vectors such that their tails have a common point for determining whether said unknown spot's vector is within said acceptable area formed by said pair of marker spot's vectors to verify that said potentially matching unknown spots indeed match; and
   said matched spot datafile comprises an exact match spot datafile for spot members having been manipulated by said verification step.

13. A method of matching protein spot patterns in a plurality of two-dimensional gel electrophoretograms, as recited in claim 10, wherein:
   said matched spots datafile comprises a composite datafile for producing a pseudo spot pattern representing the matched and unmatched spots.

14. A method of matching protein spot patterns in a plurality of two-dimensional gel electrophoretograms, as recited in claim 9, wherein said producing matching results further includes:
   generating a single reference gel based matching spot datafile;
   generating in background a multiple reference gel based matching spot datafile having contradictory spot matching data and resolving said contradiction and producing a composite matching spot datafile; and
   comparing said single reference gel based matching spot datafile with said composite matching spot datafile and further generating a potential mismatched spot members datafile and a potential matched spot members datafile for improving accuracy of said spot matching results.

15. A method of matching protein spot patterns in a plurality of two-dimensional gel electrophoretograms, as recited in claim 6, wherein:
   said logistic data and said spot physical characteristics data in said scan coordinate system comprises: gel record number, spot name, image (gel) name, x coordinates, y coordinates, integrated intensity and area.

16. A method of matching protein spot patterns in a plurality of two-dimensional gel electrophoretograms (2-D gels), said method comprising the steps of:
   (a) image scanning each of said plurality of 2-D gels and producing corresponding spot data files for each 2-D gel that contain logistic data and spot physical characteristics data in a scan coordinate system;
   (b) identifying spot members in each of said plurality of 2-D gels that bound investigative spot patterns and designating said identified spot members as marker spot members;
   (c) designating one of said plurality of 2-D gels as a reference 2-D gel, said reference 2-D gel having an associated reference spot data file including a set of reference marker spot members and unknown reference spot members having respective coordinates in said scan coordinate system;
   (d) designating at least one of remaining ones of said plurality of 2-D gels as a study 2-D gel, said study 2-D gel having an associated study spot data file including a set of study marker spot members and unknown study spot members having respective coordinates in said scan coordinate system;
   (e) performing a first transformation step that transforms positional coordinates of said set of reference marker spot members, said unknown reference spot members and each member of said set of study marker spot members from said scan coordinate system to a reference coordinate system, said first transformation step resulting in each member of said set of study marker spot members being in a registered relationship with a corresponding member of said set of reference marker spot members;
   (f) performing a second transformation step that transforms positional coordinates of each of said unknown study spot members from said scan coordinate system to said reference coordinate system, said second transformation comprising:
      (i) determining an effective range associated with each study marker spot member of said set of study marker spot members,
      (ii) determining an attraction pairing relationship between a particular study marker spot member and a particular unknown study spot member, said attraction pairing relationship being determined utilizing said effective range as determined for said particular study marker spot member,
      (iii) determining positional coordinates in said reference coordinate system of said particular unknown study spot member by adjusting original scan coordinates by shift amounts equivalent to transformation shift amounts of said particular study marker spot member that resulted from said first transformation step, and inputting said determined positional coordinates into at least one adjusted data file containing new coordinate information for all spot pattern members manipulated by said first and second transformation steps;

(iv) repeating said (ii) and (iii) steps for all unknown study spot members;

(g) repeating said steps (d), (e) and (f) on any remaining one of said plurality of 2-D gels; and (h) comparing coordinates of all spot pattern members in said at least one adjusted data file and producing results identifying matching spot pattern members.

17. A method of matching protein spot patterns in a plurality of two-dimensional gel electrophoretograms, as recited in claim 16, wherein:

said step of comparing includes the step of verifying that potentially matching unknown spots are within an acceptable vector area formed by marker spot vectors before producing said matching results;

said producing matching results includes generating a matched and unmatched spot datafiles for said unknown study spot members;

said method further includes generating a cluster datafile having contradictory matching information about certain ones of said unknown study spot members that match certain other ones of said unknown spot members in a contradictory manner; and resolving said contradictory matching information and producing spot matching results void of said contradictory matching information.

18. A method of matching protein spot patterns in a plurality of two-dimensional gel electrophoretograms, as recited in claim 17, wherein:

said unmatched spot datafile comprises a unique datafile having said unknown study spot members with coordinates that do not match with any other spot members.

19. A method of matching protein spot patterns in a plurality of two-dimensional gel electrophoretograms, as recited in claim 17, wherein:

said verification step includes a juxtaposition comparison that involves moving a constructed unknown spot's vector formed from a pair of said potentially matching unknown spots towards a pair of marker spot's vectors such that their tails have a common point for determining whether said unknown spot's vector is within said acceptable area formed by said pair of marker spot's vectors to verify that said potentially matching unknown spots indeed match; and said matched spot datafile comprises an exact match spot datafile for spot members having been manipulated by said verification step.

20. A method of matching protein spot patterns in a plurality of two-dimensional gel electrophoretograms, as recited in claim 17, wherein:

said matched spots datafile comprises a composite datafile for producing a pseudo spot pattern representing matched and unmatched spots.

21. A method of matching protein spot patterns in a plurality of two-dimensional gel electrophoretograms, as recited in claim 16, wherein:

said step of comparing includes the step of verifying that potentially matching unknown spots are within an acceptable vector area formed by marker spot vectors before producing said matching results;

said producing matching results includes generating a single reference gel based matching spot datafile and generating a multiple reference gel based matching spot datafile having contradictory spot matching data and resolving said contradiction and producing a composite matching spot datafile; and comparing said single reference gel based matching spot datafile with said multiple reference gel based datafile and further generating a potential mismatched spot members datafile and a potential matched spot members datafile for improving accuracy of said spot matching results.

22. A method of matching two-dimensional (2-D) patterns, said method comprising the steps of:

(a) image scanning a plurality of 2-D patterns and producing corresponding data files for each scanned 2-D pattern and recording logistic data and pattern physical characteristics data in a scan coordinate system;

(b) identifying pattern members in each of said scanned 2-D pattern that bound investigative patterns and designating said identified pattern members as marker members;

(c) designating one of said plurality of 2-D pattern as a reference 2-D pattern, said reference 2-D pattern having a reference pattern member data file which includes a set of reference marker members and unknown reference pattern members each having respective coordinates in said scan coordinate system;

(d) designating at least one of remaining ones of said plurality of 2-D patterns as a study 2-D pattern, said study 2-D pattern having a study pattern data file which includes a set of study marker members and unknown study pattern members each having respective coordinates in said scan coordinate system;

(e) performing at least one transformation step that transforms positional coordinates of said plurality of 2-D patterns from said scan coordinate system to a reference coordinate system for minimizing 2-D pattern preparation related distortions and generating at least one adjusted data file containing new coordinate information for all pattern members manipulated by said first and second transformation steps;

(f) repeating said steps (d) and (e) on any remaining one of said plurality of 2-D pattern;

(h) comparing physical characteristics and coordinates of all pattern members in said at least one adjusted data file and verifying that potentially matching unknown spots are within an acceptable vector area formed by marker spot vectors; and (i) producing results identifying matching pattern members.

* * * * *